US006797257B2

(12) United States Patent
McDonald et al.

(10) Patent No.: US 6,797,257 B2
(45) Date of Patent: Sep. 28, 2004

(54) PARAMAGNETIC POLYMERIZED PROTEIN MICROSPHERES AND METHODS OF PREPARATION THEREOF

(75) Inventors: Michael A. McDonald, Champaign, IL (US); Kenneth L. Watkin, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 42 days.

(21) Appl. No.: 09/976,746

(22) Filed: Oct. 12, 2001

(65) Prior Publication Data

US 2003/0003054 A1 Jan. 2, 2003

Related U.S. Application Data

(60) Provisional application No. 60/300,943, filed on Jun. 26, 2001.

(51) Int. Cl.$^7$ .......................... A61B 5/055; A61B 8/00; A61K 49/04
(52) U.S. Cl. .................... 424/9.32; 424/9.3; 424/9.322; 424/9.323; 424/9.42; 424/9.5; 424/9.51; 424/9.52
(58) Field of Search ............................... 424/9.3, 9.32, 424/9.31, 9.322, 9.323, 9.4, 9.42, 9.5, 9.51, 9.52, 489

(56) References Cited

U.S. PATENT DOCUMENTS

| | | | |
|---|---|---|---|
| 4,639,365 A | | 1/1987 | Sherry |
| 4,735,796 A | * | 4/1988 | Gordon .......................... 424/9 |
| 4,849,210 A | | 7/1989 | Widder |
| 5,215,680 A | | 6/1993 | D'Arrigo |
| 5,505,932 A | | 4/1996 | Grinstaff et al. |
| 5,508,021 A | | 4/1996 | Grinstaff et al. |
| 5,512,268 A | | 4/1996 | Grinstaff et al. |
| 5,582,172 A | | 12/1996 | Papisov et al. |
| 5,922,304 A | | 7/1999 | Unger |
| 6,193,953 B1 | | 2/2001 | Lohrmann et al. |
| 6,416,740 B1 | * | 7/2002 | Unger ....................... 424/9.52 |

FOREIGN PATENT DOCUMENTS

| | | |
|---|---|---|
| WO | WO 8502772 A | 7/1985 |
| WO | WO 9519184 A | 7/1995 |

OTHER PUBLICATIONS

Allen, et al., "Shell Waves and Acoustic Scattering from Ultrasound Contrast Agents," *IEEE Transactions On Ultrasonics, Ferroelectrics, And Frequency Control*, vol. 48, No. 2: 409–418 (Mar. 2001).

Barnhart, et al., "Characteristics of Albunex: Air–Filled Albumin Microspheres For Echocardiography Contrast Enhancement," *Investigative Radiology*, vol. 2, Suppl. 1: S162–S164 (Sep. 1990).

Bean and Livingston, "Superparamagnetism," *Journal of Applied Physics*, Supplement to vol. 30, No. 4: 120S–129S (Apr. 1959).

Bleeker, et al., "Ultrasonic Characterization Of Albunex®, A New Contrast Agent," *Journal of the Acousticsl Society of America*, vol. 87, No. 4: 1792–1797, (Apr. 1990).

Bloem and Wondergem, "Gd–DTPA as a Contrast Agent in CT," *Radiology*, vol. 171, No. 2: 578–579 (1989).

Bosquet, et al., "Gd–DOTA: Characterization Of A New Paramagnetic Complex" *Radiology*, vol. 166, No. 3: 693–698 (Mar. 1988).

Burnett, et al., "Gadolinium Oxide: A prototype Agent For Contrast Enhanced Imaging Of The Liver And Spleen With Magnetic Resonance," *Magnetic Resonance Imaging*, vol. 3, No. 1: 65–71 (1985).

Burton, et al., "Proton Relaxation Enhancement (PRE) In Biochemistry: A Critical Survey," *Progress In NMR Spectroscopy*, vol. 13: 1–45 (1979).

Chang, et al., "Second Harmonic Imaging And Harmonic Doppler Measurements With Albunex®," *IEEE Transactions On Ultrasonics, Ferroelectics, And Frequency Control*, vol. 42, No. 5: 1020–1027, (Nov. 1995).

Chin and Burns, "Predicting The Acoustic Response Of A Microbubble Population For Contrast Imaging In Medical Ultrasound," *Ultrasound in Med. & Biol.* vol. 26, No. 8: 1293–1300, (2000).

Church, "The Effects Of An Elastic Solid Surface Layer On The Radial Pulsations of Gas Bubbles," *Journal of Acoustical Society of America*, vol. 97, No. 3: 1510–1512 (1995).

Daly, et al., "MR Image Time–Intensity Relations In Spleen And Kidney: A Comparative Study of GdDTPA, Albumin–(GdDTPA), and $Gd_2O_3$ Colloid," *American Journal of Physiologic Imaging*, 5: 119–124 (1990).

Dayton, et al., "A Preliminary Evaluation of the Effects of Primary and Secondary Radiation Forces On Acoustic Contrast Agents," *IEEE Transactions On Ultrasonics, Ferroelectics, And Frequency Control*, vol. 44, No. 6: 1264–1277 (Nov. 1997).

Dayton, et al., "Optical and Acoustical Observations of the Effects of Ultrasound on Contrast Agents," *IEEE Transactions On Ultrasonics, Ferroelectics, And Frequency Control*, vol. 46, No. 1:220–232 (Jan. 1999).

(List continued on next page.)

*Primary Examiner*—Michael G. Hartley
(74) *Attorney, Agent, or Firm*—Banner & Witcoff, Ltd.

(57) ABSTRACT

The present invention relates to a composition that includes gadolinium particles encapsulated in microsphere shells. The composition is suitable for use as a contrast agent with a plurality of imaging modalities, including, for example, ultrasound, magnetic resonance imaging, and computed temography. The compositions also are useful for therapeutic applications, including neutron capture therapy.

18 Claims, 8 Drawing Sheets

OTHER PUBLICATIONS de Jong, et al., "Absorption And Scatter Of Encapsulated Gas filled Microspheres: Theoretical Considerations And Some Measurements," *Ultrasonics,* vol. 30, No. 2: 95–103 (1992).

de Jong, et al., "Higher Harmonics Of Vibrating Gas–Filled Microspheres. Part One: Simulations," *Ultrasonics,* vol. 32, No. 6, 447–453 (1994).

de Jong, et al., "Ultrasound Scattering Properties of Albunex Microspheres," *Ultrasonics,* vol. 31, No. 3: 175–181 (1993).

Forsberg, et al., "Quantitative Acoustic Characterization of A New Surfactant–Based Ultrasound Contrast Agent," *Ultrasound in Med. & Biol.,* vol. 23, No. 8: 1201–1208 (1997).

Forsberg, et al., "In Vio Evaluation of a New Contrast Agent," *Proceeding of 1994 IEEE Ultrasonic Symposium,* 1555–58 (1994).

Frinking, et al., "Ultrasound Contrast Imaging; Current And New Potential Methods," *Ultrasound in Med. & Biol.,* vol. 26, No. 6: 965–975 (2000).

Gierada and Bae, "Gadolinium As A CT Contrast Agent: Assessment In A Porcine Model," *Radiology,* 210: 829–834 (1999).

Goldberg, "Ultrasound Contrast Agents," *Clin. Diag. Ultrasound.,* 28: 35–45 (1993).

Hall, et al., Experimental Determination Of Phase Velocity Of Perfluoracarons: Applications To Targeted Contrast Agents), *IEEE Transactions On Ultrasonics, Ferroelectics, and Frequency Control,* vol. 47, No. 1: 75–84 (2000).

Havron, et al., "Heavy Metal Particulate Contrast Materials For Computed Tomography Of The Liverr," *Journal of Computer Assisted Tomography,* vol. 4, No. 5: 642–648 (Oct. 1980).

Kimura, et al., "Preparation and Characterization of Echogenic Liposome as an Ultrasound Contrast Agent," *Chem. Pharm. Bull.,* vol. 46, No. 10) 1493–96 (1998).

Lazewatsky, et al., "The Effect of Dilution Medium On The Measurement of In–Vitro Properties of Ultrasound Contrast Agents," *IEEE Ultrasonics Symposium,* 1737–1742 (1999).

Madsen, Method Of Determination Of Acoustic Backscatter And Attenuation Coefficients Independent Of Depth And Instrumentation, *Ultrasonic Scattering in Biological Tissue,* (1993).

Manry and Broschat, "FDTD Simulations for Ultrasound Propagation In A 2–D Breast Model," *Ultrason, Imaging* 18, 25–34 (1996).

Mast, et al., "Simulation of Ultrasonic Pulse Propagation Through The Abdominal Wall," *Journal of Acoustical Society of America,* vol. 102, No. 2: 1177–1190 (1997).

Mattrey and Long, "Potential Role Of PFOB In Diagnostic Imaging," *Invest Radiol,* 23(Suppl 1): S298–S301 (1988).

Mattrey, "Perfluorooctylbromide: A New Contrast Agent for CT, Sonography, and MR Imaging," *AJR* 152:247–252 (1989).

Medwin, "Counting Bubbles Acoustically: A Review," *Ultrasonics,* (1977).

Morgan, et al., "Changes in The Echoes From Ultrasonic Contrast Agents With Imaging Parameters," *IEEE Transactions On Ultrasonics, Ferroelectics, And Frequency Control,* vol. 45, No. 6: 1537–1548 (Nov. 1998).

Morgan, et al., "Experimental and Theoretical Evaluation Of Microbubble Behavior: Effect Of Transmitted Phase And Bubble Size," *IEEE Transactions On Ultrasonics, Ferroelectics, And Frequency Control,* Vo. 47, No. 6: 1494–1509 (Nov. 2000).

Niesman, et al., "Liposome Encapsulated MgCl as Liver Specific Contrast Agent for Magnetic Resonance Imaging," *Investigative Radiology,* 25: 545–51 (1990).

Quinn, et al., "Gd–DTPA: An Alternative Contrast Medium For CT," *Journal of Computer Assisted Tomography,* vol. 18, No. 4: 634–636 (Jul./Aug. 1994).

Sarkar and Prosperetti, "Coherent And Incoherent Scattering By Oceanic Bubbles," *Journal Of Acoustical Society of America,* vol. 96: 332–341 (1994).

Sarkar and Prosperetti, "Backscattering Of Underwater Noise By Bubble Clouds," *Journal of Acoustical Society of America,* vol. 93: 3128–3138 (1993).

Sarkar, et al., "Numerical Simulation Of Separated Cavitation Behind A Sphere," *ASME Cavitation Multiphase Flow Forum,* vol. 1, FED–236, 479–484 (1996).

Sarkar, et al., "Three Dimensional Numerical Simulation Of Bubble–Vortical Flow Interaction," *ASME Cavitation Multiphase Flow Forum,* FED–210, 135–143; (1995).

Sarkar & Schowalter, "Deformation Of A Two–Dimensional Drop At Non–Zero Reynolds Number In Time–Periodic Extensional Flows: Numerical Simulation," *Journal of Fluid Mechanics,* accepted (2001).

Sarkar & Schowalter, "Deformation Of A Two–Dimensional Viscous Drop In Time–Periodic Extensional Flows: Analytical Treatment," *Journal of Fluid Mechanics,* accepted (2001).

Sarkar & Schowalter, "Deformation Of A Two–Dimensional Viscoelastic Drop At Non–Zero Reynolds Number In Time–Periodic Extensional Flows," *Journal of Non–Newtonian Fluid Mechanics,* vol. 95: 315–342 (2000).

Sboros, et al., "An In Vitro Comparison of Ultrasonic Contrast Agents In Solutions With Varying Air Levels," *Ultrasound in Med. & Biol.,* vol. 26, No. 5: 807–818 (2000).

Schlief, "Echo–Enhancing Agents: Their Physics And Parmacology," *Advances In Echo Imaging Using Contrast Enhancement,* 2d ed. 85–112 (1997).

Seltzer, et al., "Hepatic Contrast Agents For Computed Tomography: High Atomic Number Particulate Material," *Journal of Computer Assisted Tomography,* vol. 5, No. 3: 370–374 (Jun. 1981).

Thakur, et al., "MR Imaging Of Pulmonary Parenchyma And Emboli By Paramagnetic And Superparamagnetic Contrast Agents," *Magnetic Resonance Imagining,* vol. 8: 625–630 (1990).

Tokumitsu, et al., "Preparation of Gadopentetic Acid–Loaded Chitosan Microparticles for Gadolinium Neutron–Capture Therapy of Cancer by A Novel Emulsion–Droplet Coalescence Technique," *Chem. Pharm. Bulletin,* vol. 47, No. 6: 838–842 (1999).

Widder, et al., "Magnetite Albumin Suspension: A Superparamagnetic Oral MR Contrast Agent," *AJR,* 149: 839–843 (Oct. 1987).

Wider, et al., "Magnetite Albumin Microspheres: A New MR Contrast Material," *AJR* 148:399–404, (Feb. 1987).

Ye, "On Sound Scattering And Attenuation of Albunex® Bubbles," *Journal of the Acoustical Society of America,* vol. 100, No. 4, part 1: 2011–2028 (Oct. 1996).

Yee, "Numerical Solution of Initial Boundary Value Problems Involving Maxwell's Equations in Isotropic Media," *IEEE Trans. Antennas Prop.,* 14(8) 302–07 (1966).

Zolle, et al., "Preparation Of metabolizable Radioactive Human Serum Albumin Microspheres For Studies Of The Circulation," *International Journal of Applied Radiation And Isotopes,* vol. 21: 155–167 (1970).

Zhou R., et al.: "Bopharmaceutics of Boronated Radiosensitizers: Liposomal Formulation of MNBOPP (Manganese Chelate of 2, 4–(Alpha, Beta–Dihydroxyethyl) Deuterioprophyrin IX) and Comparative Toxicity in Mice"; *Journal of Pharmaceutical Sciences,* American Pharmaceutical Association. Washington, US, vol. 88, No. 9, Sep. 1999, pp. 912–917.

Beall, P. et al., "Hydrogels As Oral NMR Contrast Agents and Phantom Materials", *Magnetic Resonance Imaging,* Tarrytown, NY, US, Mar. 22, 1985, p. 188.

Tuncay, M., et al., "In Vitro and In Vivo Evaluation of Diclofenac Sodium Loaded Albumin Microspheres.", *Journal of Microencapsulation,* Vo. 17, No. 2, Mar. 2000, pp. 145–155.

Brown, M., et al., "Transition Metal Chelate Complexes as Relaxation Modifiers in NMR", *Medical Physics,* vol. 11, No. 1, 1984, pp. 67–72.

Wolf, G., et al., "Time Intensity Relations in Spleen with 3 MR Contrast Agents", *Magnetic Resonance Imaging,* vo. 7, No. Suppl. 1, 1989, p. 19.

Kostler, W., et al., "Correlation of Time and Temperature Dependence of the Luminescence of Rare Earth Activated (Y, Gd)–2O–3.", *Nuclear Tracks and Radiation Measurements,* vol. 21, No. 1, 1993, pp. 135–138. International Symposium on Luminescent Detectors and Transformers of Ionizing Radiation; Riga; Latvia; Oct. 9–12, 1991.

* cited by examiner

MR Data

PARAMAGNETIC POLYMERIZED PROTEIN MICROSPHERES AND METHODS OF PREPARATION THEREOF

CROSS-REFERENCE TO RELATED APPLICATIONS

This application is based on, and claims the benefit of, co-pending U.S. Provisional Application Serial No. 60/300,943, filed on Jun. 26, 2001, and entitled "Paramagnetic Polymerized Protein Microspheres" which is incorporated herein by reference.

BACKGROUND OF THE INVENTION

1. Field of the Invention

The invention relates to contrast agents and methods of preparation thereof for use in various imaging modalities, and/or for use in therapy.

2. Description of Related Art

Introduction to Imaging Modalities

Various in vivo imaging processes, including ultrasound, magnetic resonance and computed tomography, are used as medical diagnostic tools. The underlying principle of each imaging modality is generally that the differences in a particular property or properties (e.g., acoustic properties, proton density, etc.) of the organs, tissue and other substances within the body at a location to be examined are detected and then translated into an image. The various modalities, however, rely on very different principles to generate images. The effectiveness of any of these imaging processes, and the resolution of the resulting images, in a great part depends on the degree of contrast between the body parts that the imaging equipment is able to detect so as to delineate the features of the region of interest within the subject body area. As a result, use of internally administered agents specifically designed to enhance the degree of contrast detected with a particular modality has become common. The differences in the imaging techniques involved with various modalities, however, have thus far generally restricted the use of any particular contrast agent to one imaging modality.

Ultrasound

Ultrasound ("US") is an imaging process that relies on the reflection of sound waves within the body to produce an image thereof. High frequency sound (ultrasonic) waves, which are above the range of sound audible to humans, are directed at the region of interest within the body. The waves are reflected back wherever there is a change in the physical parameters of the structures within the body, e.g., a change in density between two adjacent organs. The ultrasound equipment receives the reflected sound waves and transmits them into an image based on the differing levels of intensity of the reflected waves.

Use of a contrast agent enhances the differences in intensities of the reflected waves. For example, intravenous encapsulated microbubble contrast agents have become an established clinical tool for enhancing medical diagnostic ultrasound and Doppler sensitivity. Some current contrast agents function to enhance the appearance of the blood pool and to define its architecture and integrity. Other contrast agents provide passive, targeted, organ-specific imaging based upon the bio distribution and pharmacokinetics of the circulating contrast agent, localizing in, for example, the liver, spleen, kidney and lung.

The interaction of encapsulated microbubble contrast agents with ultrasound is complex. The microbubble response relative to a driving acoustic pressure can be divided into three categories: (1) linear scattering, (2) non-linear scattering, and (3) cavitation/destruction. Microbubbles produce linear scattering with low acoustic driving pressures and produce non-linear scattering with moderate acoustic driving pressures. At moderate acoustic driving pressures, microbubbles exhibit pressure peaks at the compressional phases of the source thereby providing both harmonic and subharmonic energy greater than the surrounding medium. At very high acoustic driving pressures microbubbles cavitate or destruct as a result of fragmentation and deflation and thus create an associated acoustic emission signal. The absolute values for low, moderate and high acoustic driving pressures are not well defined and depend upon not only the acoustic parameters of the ultrasonic source but also the constituent physical properties of the microbubbles themselves, as well as the fluid surrounding them.

A significant problem with the use of microbubble contrast agents result from the machinery associated with the imaging process. Typical medical diagnostic ultrasound imaging machinery produces acoustic pressures that can range from 0.5 to 3 mega pascals (MPa). This acoustic pressure range can destroy some microbubble contrast agents during the imaging process, thus reducing the efficacy of the contrast agent and also reducing the effective imaging time (half-life) of the contrast agent.

Albunex® (from Molecular Biosystems, of San Diego, Calif.), the first commercially available ultrasound contrast agent, is a suspension of air-filled albumin microspheres produced by sonication of a heated solution of 5% human albumin. The major drawbacks associated with use of Albunex® as a contrast agent for ultrasound are its short plasma half-life and its acoustic instability relative to pressure changes. The plasma half-life of radiolabeled Albunex® microbubbles after intravenous injection is less than one minute. In addition, backscatter intensity falls as pressure rises, an effect that has been demonstrated in vivo as a systolic fall in videointensity following intravenous injection. Moreover, albumin microbubbles cannot by used with other modalities such as magnetic resonance imaging or computed tomography because the microbubbles do not have the functional characteristics required for such modalities.

With the development of medical ultrasonic contrast agents, the theoretical behavior of encapsulated microbubbles has generated substantial interest. Ye found that at frequencies below or slightly higher than the resonance, acoustic scattering by Albunex® bubbles is nearly omni-directional and bears similarities to that by usual air bubbles. (Ye, "On Sound Scattering and Attenuation of Albunex® Bubbles," *J. Acoust. Soc. Am.*, 100(4) 2011-28, (1995)). The Ye reference also reveals that the scattering by Albunex® bubbles can be highly anisotropic when the frequency is above resonance. Work by de Jong showed large differences in non-linear behavior between ideal and Albunex® microspheres due to the additional restoring force and friction inside the shell that surrounds the Albunex® microsphere. (de Jong et al, "Higher Harmonics of Vibrating Gas-Filled Microspheres, Part One: Simulations," *Ultrasonics*, 32(6) 447-453 (1994)).

Prior efforts to address the need for an increase in the plasma half-life of medical ultrasonic contrast agents have focused on: (1) strengthening the structure of the encapsulating shell, (2) employing different substances for the encapsulating shell, or (3) chemical modification of the microsphere surface, for example, by pegylation. For example, the use of galactose with human serum albumin microspheres appears to strengthen the shell, thereby increasing the half-life to 3 to 6 minutes. (Goldberg, "Ultrasound Contrast Agents," *Clin. Diag. Ultrasound,* 28:35-45 (1993)). Kimura et al. utilized small unilamellar vesicle ("SUV"), large unilamellar vesicle ("LUV") and multilamellar vesicle ("MLV") as echogenic liposomes. (Kimura et al., "Preparation and Characterization of Echogenic Liposome as an Ultrasound Contrast Agent," *Chem. Pharm. Bull.,* 46(10) 1493–96 (1998)). The acoustic reflectivity obtained with the echogenic MLV was larger than that of the gas bubbles enclosed within a surfactant mixture. A half-lifetime of 39 minutes was observed for the MLV prepared from egg-yolk phosphatidylcholine liposomes. The duration of reflectivity was prolonged drastically to a half-lifetime of 866 minutes by incorporating cholesterol into the MLV, although, significantly, the echogenicity was decreased by such incorporation. Although there have been a number of important steps at lengthening the effective imaging half-life of injectable ultrasonic contrast agents using liposomes, there has been an overall reduction in the echogenicity of these agents.

Thus, although there are a number of ultrasonic contrast agents now available commercially, and despite significant research directed to many of these agents, limitations still exist with these agents. Furthermore, few ultrasonic contrast agents can be used with other imaging modalities.

Magnetic Resonance Another imaging technique is magnetic resonance ("MR") imaging. This modality relies on detecting the emission of electromagnetic radiation by certain atomic nuclei in the body upon application of pulsed radio frequency signals in the presence of a magnetic field. The resulting magnetic echoes produced when the signal is terminated ultimately are translated into an image.

Use of certain contrast agents with MR is known in the art. Contrast agents are commonly used intravenously to change the local magnetic field in tissue. Generally, abnormal tissue will respond differently in the presence of the contrast agent as compared to normal tissue and will give off a different magnetic echo. Thus, when the magnetic echoes are translated into an image, an image of the tissue abnormalities is provided.

The use of gadolinium oxide ($Gd_2O_3$) particles alone measuring less than 2 micrometers ($\mu m$) in diameter as a prototype MR contrast agent has been examined for imaging the liver and spleen. (Burnett et al., "Gadolinium Oxide: A Prototype Agent for Contrast Enhanced Imaging of the Liver and Spleen with Magnetic Resonance," *Magnetic Resonance Imaging,* 3:65-71 (1985)).

Another study evaluated the effects of gadolinium diethylenetriaminepentaacetic acid (Gd-DTPA), albumin Gd-DTPA, and $Gd_2O_3$ on imaging of the spleen and renal cortex. (Daly et al., "MR Image Time-Intensity Relations in Spleen and Kidney: A Comparative Study Of GdDTPA, Albumin-(GdDTPA), And $Gd_2O_3$ Colloid," *American Journal of Physiologic Imaging,* 5:119-24 (1990)). The suspension of $Gd_2O_3$ used in the studies by Burnett and Daly was synthesized by titrating a $GdCl_3$ solution with NaOH. With this method of preparation, residual $GdCl_3$ is likely to remain in the $Gd_2O_3$ preparation, such that extreme toxicity from inadvertently incorporated free $GdCl_3$ is possible. With most chelated gadolinium contrast agents, only one gadolinium atom per molecule is present in commercially-available contrast media manufactured for use in MR imaging, so that the enhancement capabilities of the contrast agent are limited. In addition, synthesis of albumin particles and also albumin microspheres tagged with gadolinium chelates on the surface would also be expected to have decreased MR sensitivity due to the limited number of sites for conjugation of the gadolinium chelate to the microsphere surface.

Magnetite ($Fe_3O_4$) albumin microspheres ("MAM") have been used as a superparamagnetic contrast agent for reticuloendothelial MR imaging. (Widder et al., "Magnetite Albumin Suspension: A Superparamagnetic Oral MR Contrast Agent," *ARJ,* 149: 839-43 (1987)). MAM was synthesized by combining 5% human serum albumin ("HSA") and magnetite to create albumin microspheres using a modified water-in-oil emulsion polymerization technique. Nonlinear behavior of MAM with increased applied external magnetic field over 0.3-0.9T was observed. The influence of magnetite on $T_2$ relaxation is believed to be due to local field inhomogeneities generated by the large magnetic moment of $Fe_3O_4$, which causes dephasing of proton spins and an acceleration of $T_2$ relaxation with negligible $T_1$ effects. Because iron oxide is predominately a $T_2$ relaxation agent, MAM has limited usefulness in conventional MR imaging. Additionally, based on the lower density of iron oxide relative to other heavy metals, iron oxide, and thus MAM, has a very limited utility for other imaging modalities, such as computed tomography.

As with contrast agents for US, contrast agents for MR also have limitations, both when used with MR and if used with other imaging modalities. Few MR contrast agents have even been evaluated for use with other imaging modalities.

Computed Tomography

Computed tomography ("CT"), also called computerized axial tomography, is an imaging modality that utilizes a toroidal, or donut-shaped x-ray camera to provide a cross-sectional image of the body area of interest. Use of certain contrast agents to improve CT images is known. Generally, the contrast agent localizes in a particular body compartment and differentially opacities normal or abnormal tissue. The contrast agent causes the tissue to inhibit passage of x-rays to produce a shadow of positive contrast in the resulting image. Iodine-based contrast agents are considered to be the industry standard with CT.

Gd-DTPA contrast agents have been used for certain limited applications in conventional angiography and CT imaging. (Bloem and Wondergem, "Gd-DTPA as a Contrast Agent in CT," *Radiology,* 171:578-79 (1989)). A major drawback associated with using Gd-DTPA contrast agents for CT imaging is the fact that only one electron dense (gadolinium) atom per molecule is present in commercially-available contrast media. In comparison, two widely used contrast agents, Optiray® (by Mallinckrodt, Inc., of St. Louis, Mo.) and Ultravist 300® (by Berlex Laboratories, Inc., of Wayne and Montville, N.J. and Richmond, Calif.), contain three electron dense (iodine) atoms per molecule. In addition, the molar concentration of gadolinium in commercially-available gadolinium-based contrast agents, such as Magnevist® (by Berlex Laboratories, Inc., of Wayne and Montville, N.J. and Richmond, Calif.), is 0.5 mol/L, which is one-fifth the molar concentration of iodine in Optiray® (320 mg of iodine per mL, or 2.5 mol of iodine per liter). Thus, presently available MR contrast agents provide sub-optimal CT enhancement and/or are not well-suited for use with other imaging modalities, such as CT and US.

Study Of Contrast Agents In Different Imaging Modalities

To date, few contrast agents have been used for imaging studies utilizing multiple imaging modalities. Correlative studies using combinations of imaging methods, most notably CT and MR imaging, are frequently performed in order to improve the accuracy of diagnosis or assess the efficacy of treatment routines. Magnevist® (Gd-DTPA) and a few other gadolinium-containing MR contrast agents have been used for this purpose, but limitations associated with the dosage and cost of commercially available MR contrast agents have prevented widespread use. Further, these agents would confer no obvious benefit to US imaging due to their low compressibility and the high concentrations required in order to provide effective US imaging.

Perfluorocarbon emulsions have been evaluated for contrast image enhancement. Perflubron (perfluorooctyl bromide, "PFOB") emulsified with egg yolk lecithin has been tested for use in US (due to its high density), MR (fluorine nuclei imaging or as a signal void for hydrogen nuclei imaging) and CT imaging (due to its bromine atom). However, neither fluorine MR imaging nor signal void imaging have found widespread use in hospital or clinical practice, where $T_1$, (and to a lesser extent, $T_2$) imaging of protons is typical. Also, PFOB is less dense radiographically, i.e. less radio opaque than iodine-based CT contrast agents, making larger doses necessary in order to achieve adequate x-ray attenuation.

Despite the significance of contrast agents in medical diagnostics and the ever-present need for correlative studies, no single commercially-available contrast agent provides effective, cost-efficient image enhancement utilizing more than one imaging modality.

BRIEF SUMMARY OF THE INVENTION

The invention relates to a new class of contrast agents, namely paramagnetic protein microspheres, for use with multiple imaging modalities. More particularly, this invention relates to gadolinium oxide albumin microspheres ("GOAM"), in both unmodified and surface-modified (including pegylation, antibody attachment, etc.) forms, that are used as contrast agents with the more widely used imaging modalities, including US, MR, and CT. In a preferred embodiment, $Gd_2O_3$ molecules are encapsulated in albumin microspheres. Unmodified and/or surface-modified GOAM of the present invention can function as contrast imaging agents for multiple imaging modalities, such as US, MR and CT.

With respect to US, these microspheres generally have the potential to withstand greater acoustic pressures than prior contrast agents due to the synthesis method used in the present invention. The presence of $Gd_2O_3$ sequestered within albumin microspheres significantly enhances echogenicity of the protein microspheres. The increased functionality of the GOAM of the present invention as a US contrast agent derives from increased echogenicity due to the effect of $Gd_2O_3$ on density, compressibility, absorption cross-section, scattering cross-section, and velocity of sound of the albumin microspheres. Additionally, toxicity may be decreased because the overall $Gd_2O_3$ concentration required for ultrasound image enhancement is reduced due to gadolinium oxide being sequestered within albumin microspheres.

The GOAM of the present invention also can provide enhanced CT imaging due to the high atomic weight and high k-edge of gadolinium. Additionally, GOAM contains multiple $Gd_2O_3$ particles, each of which are made up of several gadolinium atoms, improving the utility of GOAM as an x-ray attenuation agent for CT.

$T_1$, and $T_2$ relaxation enhancement in MR imaging is due to the paramagnetic properties of gadolinium, whose seven unpaired electrons account for its high relaxivity, and the super-paramagnetic and/or ferromagnetic properties of $Gd_2O_3$, which will be non-specifically sequestered in albumin microspheres, thereby allowing for increased interaction with mobile protons, the potential for relaxation via physical rotation of $Gd_2O_3$ and a decreased tumbling rate of $Gd_2O_3$ when associated with albumin microspheres. In addition, improved $T_1$, and $T_2$ relaxation at lower concentrations of $Gd_2O_3$ is anticipated due to the association of $Gd_2O_3$ with a macromolecule, i.e. an albumin microsphere.

GOAM also may be used in therapeutic applications, such as gadolinium neutron capture therapy, because of the high cross-sectional density and high neutron capture rate of gadolinium. Gadolinium has the highest thermal neutron capture cross-section of any known element. GOAM also may be used to encapsulate other therapeutic agents, such as antineoplastic drugs.

DETAILED DESCRIPTION OF THE INVENTION

The invention relates to paramagnetic compositions for use with various imaging modalities. More particularly, the paramagnetic compositions of the present invention comprise one or more particles selected from the group consisting of gadolinium, zinc, magnesium, manganese, calcium and compounds thereof, and one or more microsphere shells encapsulating one or more particles, wherein the composition is effective for enhancing images obtained using more than one imaging modality as compared to images obtained without the composition. The GOAM of the present invention can be used as a contrast agent during medical diagnostic imaging procedures. The composition is used with imaging techniques, including ultrasound (US), magnetic resonance (MR), computed tomography (CT) and the like, to obtain enhanced images of a selected area of a patient's body. Use of the contrast agents of the present invention allows for examination of a patient by multiple imaging techniques, without the need for multiple contrast agents or additional patient preparation between techniques, to provide correlative studies for diagnostic purposes. A method of synthesizing such compositions also is provided. Although it is contemplated that contrast agents of the present invention may include microspheres that include compounds comprising metals, such as gadolinium, zinc, magnesium, manganese, calcium and the like, it will be described by way of example principally in connection with gadolinium oxide-containing protein microspheres.

As used herein, "contrast agent" and "imaging agent" relate to any composition administered in vivo to obtain images of an area of interest of a body. The images may be obtained using any imaging technique known in the art. Preferably, use of such agent provides an enhanced image of the body structures within the area of interest as compared to an image obtained without use of any such agent.

As used herein, "microsphere" means any microbubble within a solution, the microbubble having an average diameter of no greater than about 7 $\mu$m, and more preferably between about 0.5 and about 4 $\mu$m. Generally, a microsphere may be gas-filled, aqueous or non-aqueous solution-filled and/or include particulate matter in its outer shell. Preferably, in accordance with the invention, the microsphere contains particulate matter.

As used herein, "paramagnetic compound" is intended to refer to a compound that enhances the relaxation of hydrogen protons in body tissue during MR imaging. Such a compound improves $T_1$ and $T_2$ relaxation time and readily brightens tissues in which the compound becomes localized.

Figure 1:
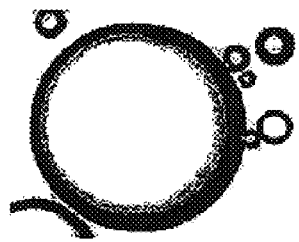
FIG. 1 is a representative image at 40× magnification of prior art unshelled air-filled microbubbles in oil.
Figure 2:
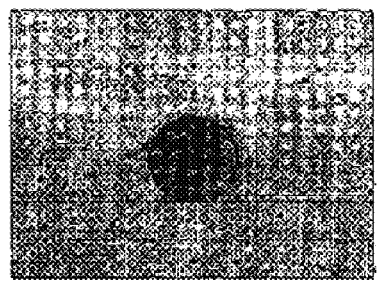
FIG. 2 is a representative image at 40× magnification of a prior art albumin microsphere.

FIG. 1 illustrates a typical air-in-oil (unshelled) microbubble, as known in the art. The oil solution was first sonicated and then air bubbles were created in the oil by blowing in air. FIG. 2 shows a prior art albumin microsphere. Similar microspheres and liposomes have been used as contrast agents with US with limited benefits. The oil microsphere of FIG. 1 and the albumin microsphere of FIG. 2 do not have the physical and functional characteristics required to provide enhancement if used with other imaging modalities, such at MR and CT.

Figure 3:
FIG. 3 is a representative image at 40× magnification of a population of $Gd_2O_3$ albumin microspheres in accordance with the present invention, showing the gadolinium particles inside of the microspheres.

As shown in FIG. 3, in accordance with the present invention, a composition of gadolinium oxide-containing albumin microspheres ("GOAM") is provided for use as a contrast agent. The contrast agent includes a high-density paramagnetic particle incorporated by polymerization in a protein shell. Preferably, the gadolinium is provided as $Gd_2O_3$ particles, with at least one encapsulated $Gd_2O_3$ particle per microsphere. Preferably, each microsphere includes a plurality of particles. Further, the gadolinium oxide preferably is present in the microspheres in spherical form. The outer shell of the microsphere may comprise proteins, such as bovine serum albumin ("BSA"), human serum albumin ("HSA"), pepsin, conjugated antibodies or antibody shells; lipids, such as phospholipids, glycolipids, and cholesterol used in some liposome preparations; gelatin; and carbohydrates, such as dextrose and dextrose-albumin, and combinations thereof, or any other substance capable of imparting the characteristics of elasticity, small size, spherical shape and having a metabolic pathway, bio distribution, and subsequent elimination pharmakokinetics. Preferably, a water-in-oil emulsion polymerization method as known to those skilled in the art may be modified to prepare the GOAM.

As an example, the GOAM may be prepared by first mixing approximately 5 grams of BSA in 10 ml of distilled water and passing the solution through a 0.2 $\mu$m filter. One gram of $Gd_2O_3$ is added to the aqueous solution. The colloid solution includes $Gd_2O_3$ particles measuring between about 50 Angstroms (Å) to about 2 $\mu$m in diameter, preferably between about 50 to about 750 Å, and more preferably between about 200 to about 400 Å. The BSA and $Gd_2O_3$ mixture is first mixed in water and then added to approximately 40 ml of oil, such as cottonseed, canola and the like, with stirring. The mixture then is sonicated at an acoustic power of 70 watts/cm$^2$ using a Misonix 2020XL sonicator fitted with a microprobe tip for up to about 5 minutes. This solution is added dropwise to about 10 ml of oil preheated to between about 100° C. and about 180° C., and heated to between about 100° C. and about 180° C. The solution is allowed to cool to room temperature with stirring. The cooled GOAM solution is separated from unused starting materials via filtered centrifugation. The resulting solution is washed in either ether, ethanol, acetone, or the like, and re-suspended in buffered saline solution or distilled water. As an example, the resulting composition may have a bubble concentration of between about $10^6$ to about $10^9$ bubbles/ml of solution and a gadolinium concentration of about 2 to about 10 mg/l (as measured via ICP analysis).

FIG. 3 illustrates microspheres having an outer protein shell surrounding a gadolinium compound. The albumin shell encapsulates particles of $Gd_2O_3$. Preferably, the $Gd_2O_3$ albumin microspheres measure between about 0.5 to about 7 $\mu$m in diameter and more preferably less than about 4 $\mu$m in diameter.

The gadolinium oxide composition of the present invention is particularly suitable for use as a contrast agent for a plurality of imaging modalities. Use of contrast agents in accordance with the present invention allows a reduced amount of gadolinium to be administered while still maintaining the image-enhancing effects of the contrast agent with MR and US imaging thereby reducing potential toxic effects associated with gadolinium.

Pegylated gadolinium oxide albumin microspheres also can be prepared from the synthesized GOAM. With pegylation, polyethylene glycol ("PEG") chains can be added to the outer shells of the microspheres. As an example, polyethylene glycol 2000 ("PEG 2000") can be attached to the GOAM using various pegylation procedures. The uptake of GOAM generally is altered, such that bio distribution of the contrast agent in soft tissues, such as the liver and spleen, changes. By surface modification of the GOAM, the half life of the contrast agent in the blood pool is increased, allowing for increased effectiveness of GOAM as a blood-pool enhancement agent.

In another embodiment of the present invention, the individual $Gd_2O_3$ particles may be pegylated and may then be encapsulated, if desired. The individual $Gd_2O_3$ particles are stabilized with a carbohydrate polyethylene glycol coat using a modified pegylation procedure. The $Gd_2O_3$ particles preferably have diameters of between about 200 to about 400 Å. Using $Gd_2O_3$ particles in this size range that have been pegylated will provide a relatively high concentration of $Gd_2O_3$ and will modify the bio distribution of the contrast agent in the body.

The contrast agents of the present invention can be used with US, MR, and CT, which will allow correlative studies to be performed. When used with US, both the microsphere shell and the encapsulated particle interact with ultrasonic waves, altering the scatter and absorption characteristics and thereby providing an enhanced image. The encapsulated gadolinium compound reacts during MR to alter the magnetic field of the tissue and acts as an absorber of x-rays during CT, thereby providing enhanced images with these modalities. The images obtained by the various modalities with the contrast agents of the present invention have increased clarity and contrast.

Use of the contrast agents provides a cost-effective means of diagnosis. The contrast agents can be used with multiple modalities, certain of which are less expensive to perform and may be used as initial indicators for diagnosis. For example, imaging with US is not as costly as with MR, and US may be conducted prior to MR or other techniques to provide an initial diagnosis, such that subsequent, more costly, tests may be more focused or possibly avoided.

The contrast agents of the present invention also may be used for certain therapeutic applications. More particularly, gadolinium oxide-containing microspheres can be used with neutron capture therapy in the treatment of cancer. Any procedure for neutron capture therapy known to those of skill in the art may be modified in accordance with the present invention. Generally, the composition of gadolinium oxide-containing microspheres can be prepared as described above. The gadolinium composition is administered intravenously and/or otherwise localized to a tumor. When the gadolinium nucleus is irradiated with neutrons, the gadolinium produces several forms of radiation, including γ-rays, x-rays, internal conversion electrons and Auger electrons, which help to kill the tumor. Because $Gd_2O_3$ has a very large thermal neutron capture cross-section (66 times larger than that of boron-10), the range of radiation and the corresponding killing efficacy are increased when compositions in accordance with the present invention are used.

In accordance with the present invention there is also provided a mathematical model that is free from certain limitations of the models currently being used for contrast agents. Additionally, the model is implemented into a simulation tool to characterize newly created multimodal agents and thereby to evolve improved designs with optimal characteristics.

A two-component simulation model is provided. The first part uses Boundary Element Method ("BEM") to solve for the potential flow. The second part uses a Finite Difference Time Domain ("3D-FDTD") model. This model uses the results of the BEM model to simulate the bulk behavior of encapsulated microbubbles in solution insonified by pulsed ultrasound waves. The 3D-FDTD method is used for the simulation of acoustic wave propagation and scattering in inhomogeneous media. This method exploits the true three-dimensional aspect of the propagation problem by iteratively solving in time steps the equation of motion and the equation of continuity of the acoustic wave in the form of difference equations, hence the name Finite Difference Time Domain ("FDTD"). The advantage of the FDTD method is the ability to simulate complex structures in the time domain. This is especially important when dealing with biological structures. In addition, transient behavior as well as steady state behavior also can be studied with this method.

Although not always explicitly stated, the near field has always been modeled with incompressible potential flow assumption (radial velocity approximately $1/r^2$ at a distance r from the bubble center). The multi-scale rigorous mathematical model of the present invention considers an inner potential region near the bubble and an outer acoustic region far away. Rather than using a radial equation, a boundary element method is applied to solve for the potential flow in the near field, which furnishes nonlinear shape oscillation and, therefore, the directional information of the pressure and the velocity field around an agent. The velocity potential $\Phi(x)$ is obtained by solving the discretized integral equation:

$$\phi(x) = \int_S \phi(x_0)\frac{\partial G}{\partial n}(x-x_0)dS(x_0) - \int_S G(x-x_0)\frac{\partial \phi}{\partial n}(x_0)dS(x_0) \quad 15$$

where $(x,x_o)$ is the Green's function of the Laplace equation $-[4\pi|x,x_0|]^{-1}$. The pressure and the velocity fields obtained at the inscribing surface, $\partial\Omega_s$, are used to compute the scattered far field in the acoustic region. In the far field the flow is compressible yet linear:

$$(\nabla^2 + k_m^2)\phi(x) = 0$$

where $k_m$ is the wave number based on the effective sound speed in the medium containing agents. This equation is solved for the velocity, $\partial\Phi/\partial n$, given the values of $\Phi$ at the surface. On the other hand, $\Phi$ at the surface is obtained by the Bernoulli's equation, valid in a potential flow:

$$\frac{\partial \phi}{\partial t}(x) + \frac{1}{2}|\nabla \phi(x)|^2 = \frac{p_\infty - p_L}{\rho}$$

The effects of internal pressure due to vapor (υ) and gas (g) and surface tension (σ) are represented in the liquid pressure $p_L$ at the outer wall of the agent:

$$p_L = p_v + p_g - C\sigma$$

C being the curvature of the bubble surface.

Most contrast agents are made with an encapsulating shell, however, very little is known about shell properties, which vary in thickness, number of layers and other characteristics, depending on the method used to create them. As mentioned before, various models have been proposed with various degrees of detail for the elastic shell. In Church's solution it is assumed that a continuous layer of incompressible, solid elastic material separates the gas from the bulk Newtonian liquid. A Rayleigh-Plesset-like equation describing the dynamics of such surface-contaminated gas bubbles was derived. Church found that the resonance frequencies of individual bubbles tend to increase as the modulus of rigidity increases. Encapsulated bubbles with shell rigidity greater than approximately 85 mega pascals (MPa) provide a greater cross section per unit attenuation in the lower biomedical frequency range than do free bubbles of the equivalent size.

The need to simultaneously incorporate both non-linearity and directionality is addressed by the present model. Non-linearity is essential for harmonic and transient power scattering, both of which promise better discrimination against background tissue signals. On the other hand, directionality is an important observed effect leading to significant modification of the contrast response. This is especially important in the development of medical imaging contrast agents in general and most specifically with acoustic contrast agents.

The output from the boundary element model is used for the input of the propagation model as described below.

Microbubbles in solution undergo nonlinear radial oscillation when they are exposed to moderately strong (greater than 100 KPa) ultrasound waves. These oscillations produce echoes containing second and higher harmonics of the incident wave.

The pressure and the particle velocity in the coupled wave equations are the instantaneous total pressure and the total particle velocity at any point in the fluid medium. The equations for a lossless medium with variable speed and density are the following:

$$\nabla p(x,y,z,t) = -\rho(x,y,z,t) \partial u(x,y,z,t)/\partial t, \quad (1)$$

$$\nabla u(x,y,z,t) = (-1/(\rho(x,y,z,t)c^2))(\partial p(x,y,z,t)/\partial t) \quad (2)$$

The information needed to completely compute the different fields over time is the initial fields' distribution and the incident wave satisfying the two coupled equations. For the computation, the fields in the medium are set to zero at the initial time t=0. The two coupled equations are discretized to obtain the FDTD equations. The practical implementation of the FDTD method starts by partitioning the entire 3D space into small cubes following the Yee cell method. (Yee, "Numerical Solution of Initial Boundary Value Problems Involving Maxwell's Equations in Isotropic Media," *IEEE Trans. Antennas Prop.*, 14(8) 302-07 (1966)). Building a medium consists of labeling each cube so that a given scattering medium with specific material properties is obtained. The computational complexity of the problem is $O(n^3)$ and the storage requirement is also $O(n^3)$ where n is the number of cells on each side of a cubic geometry. The transducer is modeled as ideal point sources, generating a Gaussian spherical wave that propagates through the 3D medium. The architecture of the code is simple given the modular nature of each subroutine. Parallel processing can be used for larger medium simulation. The procedure for the simulations are: (1) generate the synthetic medium, (2) compute analytically the propagation of the incident field in the medium, and (3) compute the scattered pressure field and the scattered velocity field at each point in the medium.

The FDTD method can predict field disturbances due to short-range variations in medium density of the order of the wavelength of the incident wave. Applications for this method include the prediction of the acoustic field distribution in inhomogeneous media such as biological tissues, prediction of encapsulated microbubbles, insonification in different regimes, tissue characterization and blood flow. Synthetic media can be generated and used to compute the different scattered fields for analysis. Additionally, this method also can be used by first experimentally obtaining the medium parameters, i.e., by reconstruction, or from knowledge of anatomy of the given tissue, and then computing the various acoustic fields for specific studies.

EXAMPLES

The following examples are intended to illustrate the invention and not to limit or otherwise restrict the invention.

Example 1

Ultrasound Studies

Figure 4A:
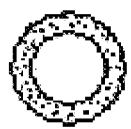
FIG. 4a illustrates a cross-section of a plastic tube taken at one end of the tube.
Figure 4B:
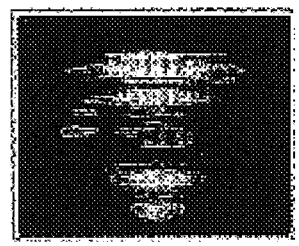
FIG. 4b is a representative image of the plastic tube of FIG. 4a using B-mode ultrasound of oil.
Figure 4C:
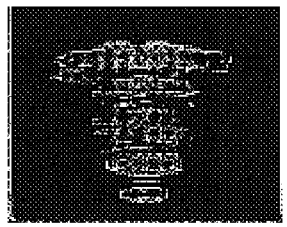
FIG. 4c is a representative image of the plastic tube of FIG. 4a using B-mode ultrasound of air-filled albumin microspheres in oil.
Figure 4D:
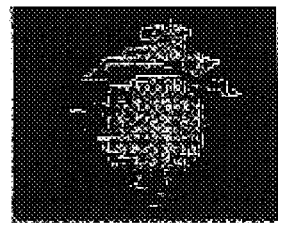
FIG. 4d is a representative image of the plastic tube of FIG. 4a using B-mode ultrasound of GOAM in oil.
Figure 5A:
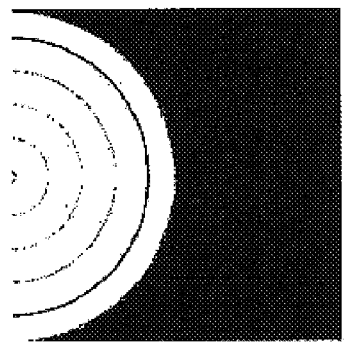
FIG. 5a is a representative image of a simulation illustrating total wave in the plane xz through the center of the sphere, from left to right, at a time of 11.5 microseconds.
Figure 5B:
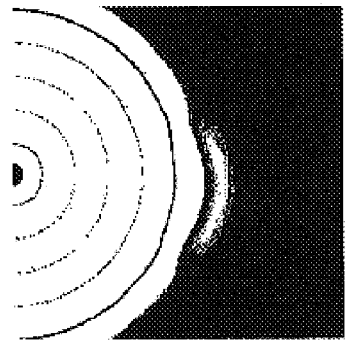
FIG. 5b is a representative image of the simulation of FIG. 5a at a time of 17.3 microseconds.
Figure 5C:
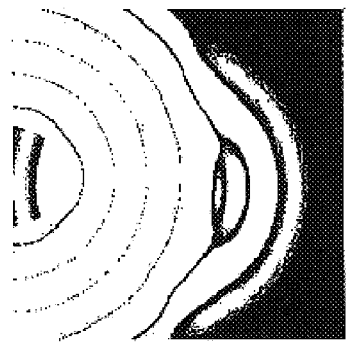
FIG. 5c is a representative image of the simulation of FIG. 5a at a time of 23.1 microseconds.
Figure 5D:
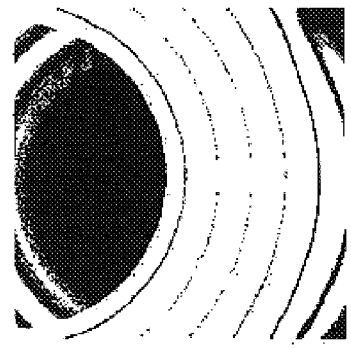
FIG. 5d is a representative image of the simulation of FIG. 5a at a time of 38.4 microseconds.
Figure 6:
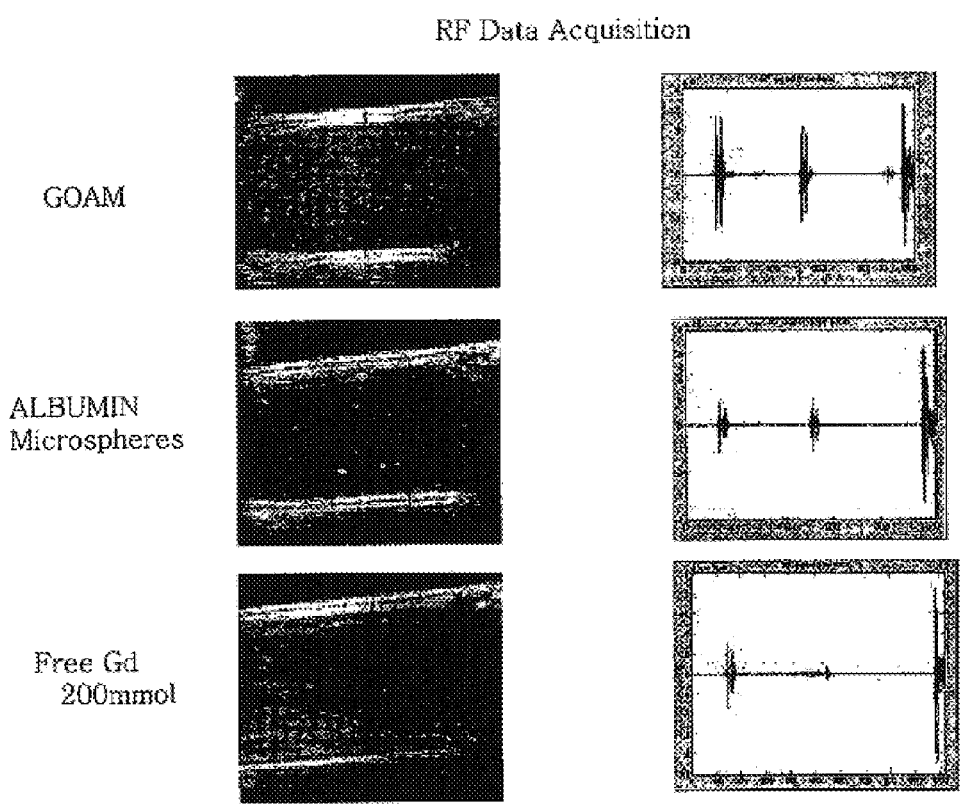
FIG. 6 illustrates RF acquisition data comparing GOAM of the present invention, albumin microspheres, and free $Gd_2O_3$.
Figure 7:
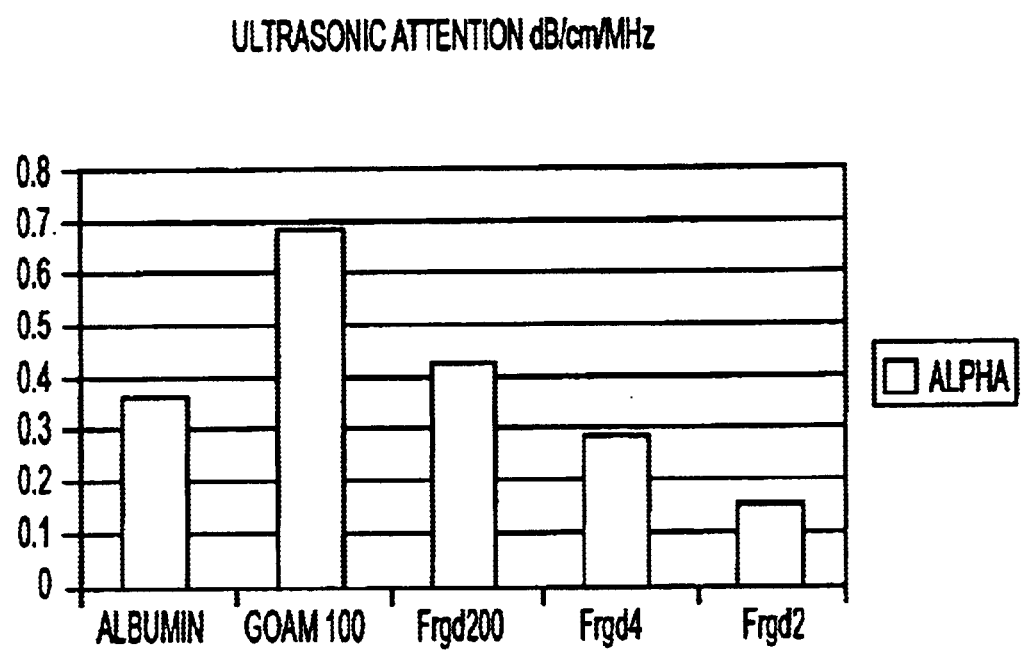
FIG. 7 illustrates ultrasonic attenuation comparing GOAM of the present invention, albumin microspheres, and free $Gd_2O_3$ at three separate concentrations.

Preliminary imaging studies were conducted to compare the cross-sectional ultrasound images of oil (containing no contrast agents), air-filled albumin microspheres, and unmodified and surface-modified GOAM flowing through a tube. An Aloka SSD5500 PHD ultrasound machine with a linear transducer (UST 5539 10 MHz) was used to create traditional B-mode ultrasound images. In these experiments, the above solutions were injected into clear plastic Tygon tubing (OD=0.318 cm; ID=0.159 cm) (FIG. 4a) immersed in degassed water at room temperature. Cross-sectional images of the tube were captured using a personal computer, video frame grabber and real time video capture software (Capture©, Watkin, 1997). These images are shown in FIGS. 4b–4d.

These images clearly demonstrate the full circumference visualization capabilities of the various media—oil (no contrast media), air-filled albumin microspheres, and GOAM. Differences are clearly evident in the cross-sectional B-mode ultrasound images. The inner circumference of the tube is not visible when imaging with oil, which does not contain contrast media. Imaging with flowing (and static) air filled albumin microspheres enhances the tube image but the fall circumference of the tube is not visible. GOAM provides fill circumferential tube delineation and enhancement. This demonstrates the potential utility of modified GOAM for mapping of blood vessels, especially the delineation of small blood vessels. Modified GOAM has the potential to enhance visualization of flow in small vessels of the heart and perhaps enhance low velocity ultrasound spectral Doppler signals. Moreover, full vessel circumference imaging is an essential prerequisite to 3D imaging studies.

Example 2

Physical Characterization of Unmodified and Surface-Modified GOAM

The determination of the size distribution, concentration, and size fractionation of the synthesized GOAM is accomplished via Coulter counter analysis. In addition, optical microscopic images (Bausch & Lomb) are used to verify the size and conformation of GOAM.

Example 3

Acoustic Simulations

Two different simulation approaches are required to describe the characteristics of the acoustic driving forces on the developed microsphere as well as the acoustic propagation of the scattered ultrasonic energy. One approach uses boundary element method (BEM) modeling to describe the acoustic behavior of the microsphere. Finite difference time domain modeling (FDTD) is used to examine the backscattering properties of the reflected acoustic pressure waves.

Example 4

Ultrasound Characterization of Unmodified and Surface-Modified GOAM

General Procedures The in vitro ultrasonic characteristics of synthesized unmodified or surface-modified GOAM are determined at different concentrations of $Gd_2O_3$ at constant temperatures. The following characteristics are determined: bubble size-distribution, life time, effect of ultrasound machine power, effect of suspension condition—dilution and carrier medium, attenuation (as a function of frequency), sound velocity, normalized backscatter coefficient, and scattering.

The acquisition of all ultrasound signals is accomplished using an Aloka 5500 PHD RF machine using two different ultrasound transducers (Aloka UST 5539 10 MHz linear small parts transducer and Aloka UST 9119 2-5 MHz curvilinear abdominal transducer). The Aloka 5500 PHD RF stores simultaneously, in real time, multiple frames of RF data from all the transducer elements as well as the corresponding B-mode images. These data are then ported to a PC (Intel 800 MHz PIII) for off-line analyses of the independent RF element data as well as the associated B-mode images.

Forward scattering data acquisition is accomplished using a high performance needle hydrophone data acquisition system (Precision Acoustics, Ltd. Digital Acquisition System) with a 0.04 mm 9 micron PVDF probe). These data are stored on a personal computer.

A Bausch and Lomb optical microscope is used to acquire digitized optical images of the microbubbles. Digital image acquisition is accomplished using a Sony CCD camera (Model 1250) linked to a Pinnacle Systems video frame grabber board (Miro DC30 plus) and a PC (Intel 800 MHz PIII) and stored on the hard drive. All images are acquired in RGB mode with an image size of 608×456 pixels. Specially developed image capture software (Capture©, Watkin, 1998-2001) permits real time image capture at 30 fps.

Both in vitro and in vivo B-mode imaging data are simultaneously recorded using a separate computer acquisition system. Digital image acquisition is accomplished using a Pinnacle Systems video frame grabber board (Miro DC30 plus) and a PC (Intel 800 MHz PIII) and stored on the hard drive. All images are acquired in RGB mode with an image size of 608×456 pixels. Specially developed image capture software (Capture ©, Watkin, 1998-2001) permits real time image capture at 30 fps. This acquisition system is connected directly to the color video output of the Aloka 5500 PHD RF machine.

An acrylic imaging tank, (25 cm×15 cm×15 cm) with a 10 cm×10 cm thin membrane window at one end for acoustic monitoring is filled with freshly degassed, de-ionized water at constant temperature (22° C.). Ready-to-use cellulose dialysis tubes (240 μm) are fixed across the width of the imaging tank at 1 cm, 2 cm and 3 cm depths from the imaging window. These tubes are filled with the contrast media selected for each experiment. Rinsing protocols are used following the injection of each contrast media.

Bubble Size-distribution

Two different methods are used to determine the size and distribution of the unmodified and surface-modified GOAM. An optical microscope is used for optical verification of the sizes and distributions of the microbubbles at 10× and 40× power. Calibration is provided by precision graticule slides.

More precise bubble sizing and distribution data is determined using a Beckman-Coulter Multisizer Z2.

GOAM Life Time

The echogenicity of unmodified and surface-modified GOAM is tested over an extended period of time to assess the time period during which GOAM remain stable within a specially constructed imaging vial. A small imaging vial with a thin acoustic membrane is used for this purpose. Ultrasound imaging acoustic power is fixed at a mechanical index of 0.7. A fixed concentration of microbubbles is used. The concentration is in the linear range of the backscatter/concentration plot.

Effects of Acoustic Power

Ultrasound pressure waves of current B-mode imaging machines typically destroy microbubbles. Fixed concentrations of the contrast agent are stabilized in cellulose dialysis tubes to determine the characteristics of unmodified and surface-modified GOAM in a commercial diagnostic ultrasonic field. The two different ultrasound transducers described above are used to acquire the RF data and B-mode images. The acoustic power of the ultrasound machine as reflected by the mechanical index ("MI") provided on the machine is set in 0.1 MI steps, from 0.2 to 0.8 MI. The tube contains fresh contrast agents for each MI level test for each transducer. The backscatter coefficient for each step for each contrast agent is determined.

Effects of Suspension Condition

Different suspension conditions affect the properties of ultrasound contrast agents. The effects are tested by changing different air concentrations, diluting the contrast agent, and utilizing different carrier media.

The effects of air concentration are assessed for both unmodified and surface-modified GOAM at fixed concentrations using the methods described in Sboros. (Sboros et al., "An In Vitro Comparison of Ultrasonic Contrast Agents in Solutions with Varying Air Levels," *Ultrasound in Med. & Biol.*, 26:807-18 (2000) which is incorporated by reference herein). Sterile water is used as the suspension medium. A sterile bag filled with sterile water is infused with helium or air to achieve partial oxygen pressures ($pO_2$) of 1.5 or 24.7 kPa, respectively. These suspensions are injected slowly in the cellulose dialysis tubing. The imaging data is gathered under these conditions using the Aloka 5500 PHD RF machine to acquire the RF data and B-mode images. Microbubble concentration and size are determined for the suspensions. Normalized ultrasonic backscatter vs. concentration is examined.

In vitro characterization of ultrasonic contrast media conducted in aqueous solutions do not necessarily adequately simulate the behavior of contrast agent in the circulatory system. Therefore, different concentration levels of GOAM are suspended with sterilized water, saline, plasma and whole blood at 37° C. The contrast agent is suspended in an imaging cell similar to that described by Lazewatsky and colleagues. (Lazewatsky et al., "The Effect of Dilution on the Measurement of In-vitro Properties of Ultrasound Contrast Agents," *Proceeding of 1999 IEEE Ultrasonics Symposium*, 1737-42 (1999) which is incorporated by reference herein). The two different ultrasound transducers described above are used to acquire the RF data and B-mode images. Time-video intensity along with backscatter data are acquired using the video and RF data acquisitions systems described above.

Attenuation as a Function of Frequency

The in vitro enhancement and attenuation properties of unmodified and surface-modified GOAM are examined using the methods described by de Jong (de Jong and Hoff, "Ultrasound Scattering Properties of Albunex® Microspheres," *Ultrasonics*, 31(3) 175-81 (1993) which is incorporated by reference herein) and by Forsberg et al. (Forsberg et al., "In Vio Evaluation of a New Contrast Agent," *Proceeding of 1994 IEEE Ultrasonics Symposium*, 1555-58 (1994); "Quantitative Acoustic Characterization of a New Surfactant-Based Ultrasound Contrast Agent," *Ultrasound in Med. & Biol.*, 23:1201-08 (1997) which both are incorporated by reference herein) using a flow pump to provide flow through the dialysis tubing in the imaging tank described above. Frequency dependent dose attenuation is determined, as well as the time-attenuation dose dependence curves.

Sound Velocity

Because unmodified and surface-modified GOAM have particulate gadolinium encased within the microbubble, it is important to determine the effects of the embedded gadolinium on microbubble sound velocity. Different concentrations of GOAM are utilized for this test. A modified version of the displacement method described by Hall et al. (Hall et al., "Experimental Determination of Phase Velocity of Perfluorocarbons: Application to Targeted Contrast Agents," *IEEE Transactions on Ultrasonics, Ferroelectrics and Frequency Control*, 47:75-84 (2000) which is incorporated by reference herein) is employed. The imaging tank described above is employed along with the cellulose tubing. A polished stainless steel plate is placed 0.5 cm behind the cellulose tube. The two different ultrasound transducers described above are used to acquire the RF data and B-mode images. The tube is filled with sterilized water. Then the tube is filled with different concentrations of the contrast agents. Full rinsing is conducted between each injection of different contrast media. Sound velocity for each concentration is determined.

Scattering

Because unmodified and surface-modified GOAM have particulate gadolinium encased within the microbubble, it is also important to determine the effects of the embedded gadolinium on microbubble directional scattering. Different concentrations of GOAM are utilized for this test. The two different ultrasound transducers described above are used to acquire the RF data and B-mode images The cellulose tube is filled with sterilized water first. Then the tube is filled with different concentrations of the contrast agents. Full rinsing is conducted between each injection of different contrast media. A needle hydrophone (Precison Acoustics Ltd.) is utilized to record the acoustic wave at 45°, 90°, 135° and 180° relative to the circumference of cellulose tubing.

Blood Flow Imaging

The dynamic blood flow imaging characteristics of different concentrations of unmodified and surface-modified GOAM are examined using sterile water, plasma, and whole blood. Two different flow systems are used. The first consists of a tissue mimicking flow phantom (ATS Laboratories, Bridgeport, CT) with a 6 mm diameter flow channel for simulating large vessels. The second system utilizes the tank and cellulose tubing apparatus described above which simulate smaller capillaries. (This system lacks a tissue mimicking interface.) A precision flow pump provides both constant and pulsatile flows. These imaging data are recorded directly on to the hard disk of a PC using the color video output of the Aloka 5500 PHD connected to the image acquisition system described above. The effects of different concentrations on the spectral Doppler signals from the Aloka 5500 are examined along with the effects on both color Doppler and "Power Flow" imaging in B-mode.

Example 5

MR Characterization $T_1$ and $T_2$ relaxation are determined for unmodified and surface-modified GOAM, GOAM made from pegylated $Gd_2O_3$ colloid solution, $Gd_2O_3$ colloid solution and GOAM having encapsulated pegylated $Gd_2O_3$ at various concentrations using different pH and temperatures. Imaging of the above reagents is conducted in sterile water, plasma, and whole blood in order to better approximate physiological conditions.

Images are obtained on a 3.0T imaging spectrometer with image processing and display system. A partial saturation pulsing sequence is utilized for $T_1$ weighted 2D acquisitions. $T_1$ values are derived by an inversion recovery method and curve fitted by the least squares techniques (i.e. Niesman et al., "Liposome Encapsulated MgCl as Liver Specific Contrast Agent for Magnetic Resonance Imaging," *Investigative Radiology,* 25:545-51 (1990) which is incorporated by reference herein). $T_2$ values are derived by the Carr-Purcell-Meiboom-Gill pulse sequence with curve fitting by the least squares method.

Additional studies involve measurement of $T_1$ and $T_2$ relaxation at different magnetic field strengths using a 3T spectrometer.

Example 6

Simulation of Ultrasound Wave Propagation

Ultrasound wave propagation in a synthetically generated medium was simulated. The simulation consisted of a bubble with an outer diameter of 250 $\mu$m and inner diameter of 225 $\mu$m. The bubble was surrounded by an albumin shell of thickness 12.5 $\mu$m. FIGS. 5*a*-5*d* illustrate a sequence of snapshots of the absolute value of the scattered wave. The simulation shows the progress of an ultrasound wave toward a single spherical target. FIGS. 5*a*-5*d* illustrate that the ultrasonic wave hitting the sphere, as well as the wave being reflected (the backscattered wave), is accurately simulated.

Example 7

CT Characterization

CT attenuation of unmodified and surface-modified GOAM, GOAM made from pegylated $Gd_2O_3$ colloid solution, $Gd_2O_3$ colloid solution and GOAM having encapsulated pegylated $Gd_2O_3$ at various concentrations, as well as the lowest dose providing acceptable enhancement are determined. Serial dilutions of the above reagents in normal saline or distilled water are placed in a tissue equivalent phantom and positioned in the center of the gantry of the CT scanner. The phantom containing the above reagents is imaged under the following constant scanning parameters: slice thickness of 10 mm, 120 keV, 250 mA, scan time of 1 second and a 25 cm field of view. Attenuation measurements obtained from region of interest circles of approximately 80 mm3 (10 mm thickness) are plotted against the concentrations of the reagents, and a linear regression analysis is performed. The attenuation of each dilution is recorded as mean Hounsfield units using region of interest analysis.

Example 8

RF Data Acquisition

FIG. 6 illustrates RF acquisition data for B-mode ultrasound imaging comparing GOAM of the present invention, air-filled albumin microspheres, and free $Gd_2O_3$. The photographs in the left column show an ultrasound image of a cross-sectional view of a 1.5 ml eppendorf tube on its side and having either GOAM, albumin microspheres or free $Gd_2O_3$ contained within. The GOAM solution has a bubble concentration of $10^6$ bubbles/ml and a $Gd_2O_3$ concentration of 0.02 mmol. The albumin microspheres solution has a bubble concentration of $10^6$ bubbles/ml. The free $Gd_2O_3$ has a concentration of 200 mmol. To the right of each image is a plot of RF data illustrating amplitude over time as the ultrasound wave passed through the eppendorf tube from the top, through the contrast agent and then through the bottom. This test demonstrates that GOAM provides much greater RF attenuation than the other contrast agents.

Example 9

Ultrasonic Attenuation

As shown in FIG. 7, ultrasonic attenuation of GOAM of the present invention is compared to that of air-filled albumin microspheres, and free $Gd_2O_3$. Ultrasonic attenuation (dB/cm/MHz) is plotted for albumin microspheres (bubble concentration of $10^6$ bubbles/ml), GOAM (bubble concentration of $10^6$ bubbles/ml and $Gd_2O_3$ concentration of 0.02 mmol), and free $Gd_2O_3$ at concentrations of 200 mmol, 4 mmol and 2 mmol, respectively. This test demonstrates that GOAM has greater ultrasonic attenuation than the other contrast agents.

Example 10

Integrated Ultrasonic Backscatter Coefficient

Figure 8:
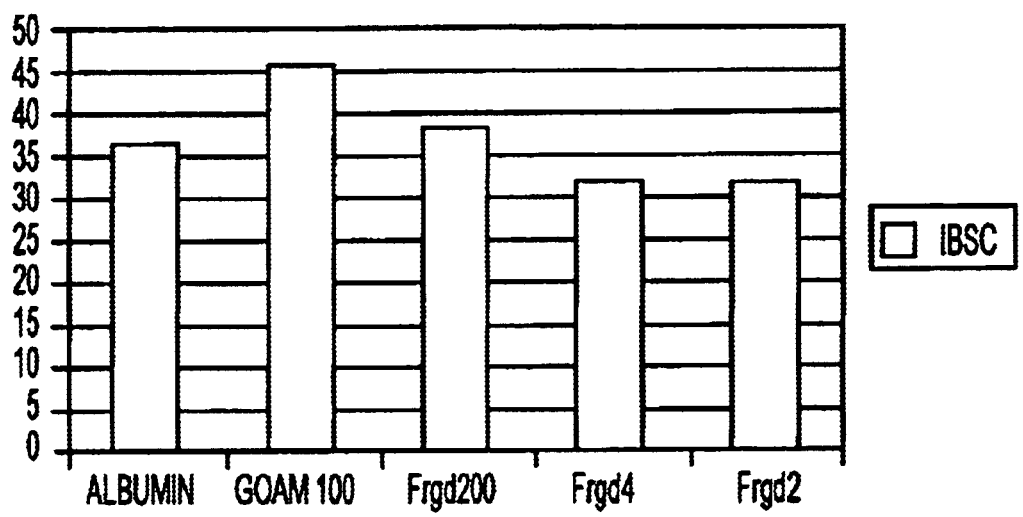
FIG. 8 illustrates integrated ultrasonic backscatter coefficient comparing GOAM of the present invention, albumin microspheres, and free $Gd_2O_3$ at three separate concentrations.

As shown in FIG. 8, the ultrasonic backscatter coefficient of GOAM of the present invention, air-filled albumin microspheres, and free $Gd_2O_3$ at three separate concentrations is compared. The integrated ultrasonic backscatter coefficient (dB) is plotted for albumin microspheres (bubble concentration of $10^6$ bubbles/ml), GOAM (bubble concentration of $10^6$ bubbles/ml and $Gd_2O_3$ concentration of 0.02 mmol), and free $Gd_2O_3$ at concentrations of 200 mmol, 4 mmol and 2 mmol, respectively. This test demonstrates that GOAM has a greater integrated ultrasonic backscatter coefficient than the other media.

Example 11

Second MR Characterization

Figure 9:
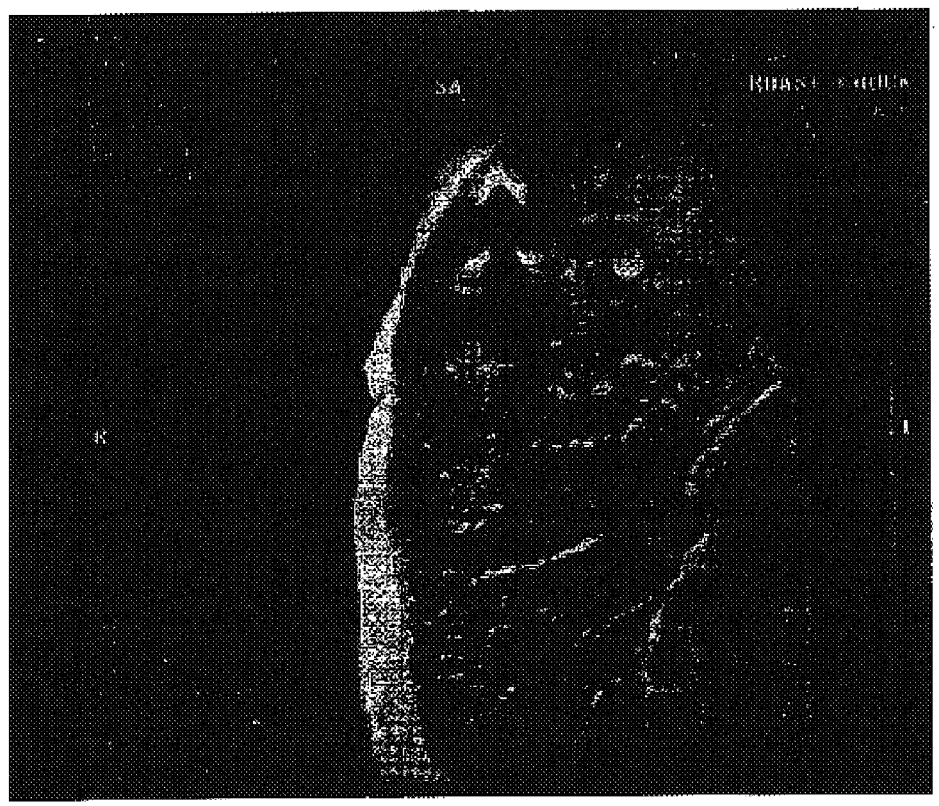
FIG. 9 illustrates $T_1$ magnetic resonance enhancement by various contrast agents, including GOAM of the present invention.

FIG. 9 illustrates magnetic resonance enhancement of various contrast agents. Vials containing the various contrast agents (or water) were inserted into a portion of beef. The contrast agents included, starting from the top row, from right to left, moving down:

First (top) row: Isovue® 300 (by Bracco Spa of Italy) (788 nmmol), ProHance® (by Bracco Spa of Italy) (500 mmol);

Second row: Free $Gd_2O_3$ (20 mmol, 100 mmol and 200 mmol, respectively);

Third row: Free $Gd_2O_3$ (0.02 mmol, 0.4 mmol and 1.0 mmol, respectively); and

Fourth (bottom) row: Water, Air-filled albumin microspheres and GOAM of the present invention (bubble concentration of $10^6$ bubbles/ml and $Gd_2O_3$ concentration of 0.02 mmol).

This test demonstrates that GOAM provides enhanced MR imaging.

Example 12

CT Characterization

Figure 10:
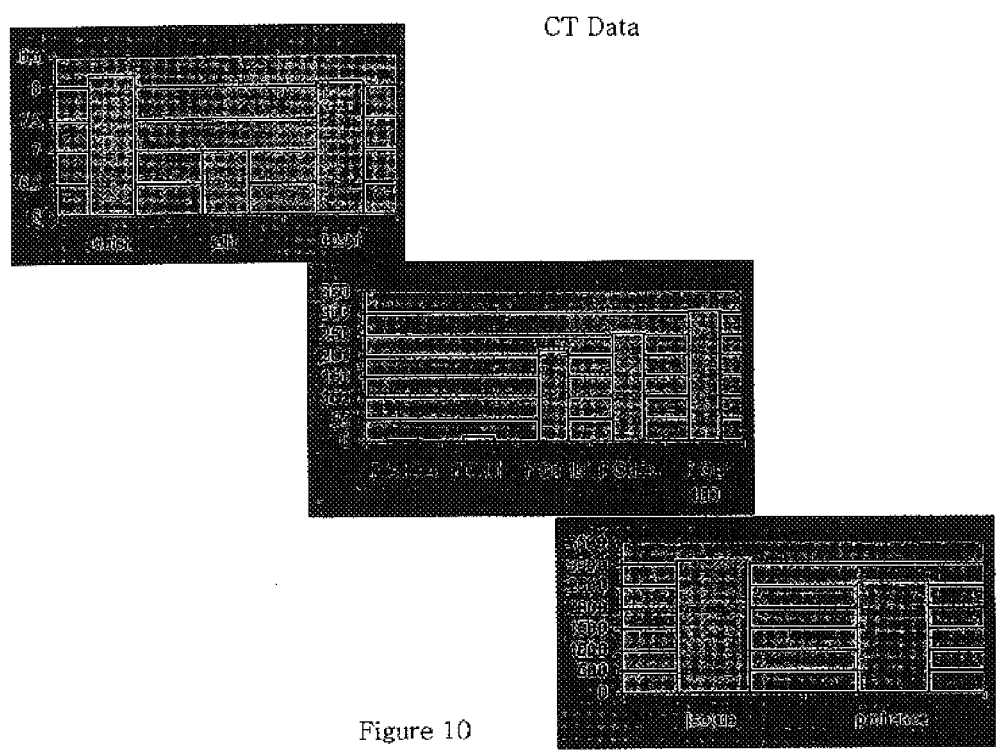
FIG. 10 illustrates CT attenuation comparing GOAM of the present invention, water, albumin microspheres, free $Gd_2O_3$ at various concentrations, and stock solutions of commercially available contrast agents.

FIG. 10 illustrates CT attenuation comparing GOAM of the present invention, water, albumin microspheres, free $Gd_2O_3$ at various concentrations, and commercially available contrast agents. CT attenuation (Hounsfield units) is plotted for water, albumin microspheres (bubble concentration of $10^6$ bubbles/ml), GOAM (bubble concentration of $10^6$ mmol, 1.0 mmol, 10 mmol, 20 mmol, and 100 mmol, respectively, Isovue® 300 (by Bracco Spa of Italy) (788 mmol) and ProHance® (by Bracco Spa of Italy) (500 mmol). This test demonstrates that GOAM has greater CT attenuation as compared to albumin microspheres. Additionally, this test suggests that attenuation will increase as greater concentrations of $Gd_2O_3$ are incorporated into the GOAM.

Many modifications and variations may be made in the techniques and compositions described and illustrated herein without departing from the spirit and scope of the present invention. Accordingly, the techniques and compositions described and illustrated herein should be understood to be illustrative only and not limiting upon the scope of the present invention.

What is claimed:

1. An imaging composition for obtaining images by medical diagnostic imaging procedures comprising in combination:

one or more particles comprising gadolinium oxide; and one or more microsphere shells including a protein comprising albumin each shell having an inner wall and an outer wall and encapsulating the one or more particles between the inner and outer walls, one or more said microsphere shells having an average diameter of no more than about 70,000 Å, the composition effective in a single dose without administration of additional doses of an imaging composition in an in vivo administration for obtaining images using more than one imaging modality.

2. A composition in accordance with claim 1, wherein said particles are spherical.

3. A composition in accordance with claim 2, wherein said particles have diameters of no more than about 450 angstroms.

4. A method of obtaining images using medical diagnostic imaging modalities comprising:

administering in vivo an imaging composition comprising a suspension of microsphere shells including a protein comprising albumin and having inner and outer walls encapsulating between the inner and outer walls one or more particles comprising gadolinium oxide, the imaging composition administered in an amount effective for obtaining images using two or more imaging modalities;

obtaining a first image using a first imaging modality selected from the group consisting of ultrasound, magnetic resonance and computed tomography; and obtaining a second image using a second imaging modality different from the first imaging modality without administration of an additional amount of the imaging composition or an amount of another imaging composition to obtain the second image.

5. A composition in accordance with claim 1, wherein said particles have diameters of between about 50 Å and about 20.000 Å.

6. A composition in accordance with claim 5, wherein said particles have diameters of between about 50 Å and about 750 Å.

7. A composition in accordance with claim 6, wherein said particles have diameters of between about 200 Å and about 400 Å.

8. A composition in accordance with claim 1, wherein said microsphere shells have an average diameter between about 5,000 Å and about 40,000 Å.

9. A composition in accordance with claim 1, wherein one or more particles are pegylated.

10. A composition in accordance with claim 9, wherein said particles have diameters of between about 200 Å and about 400 Å.

11. A composition in accordance with claim 1, wherein the albumin is selected from the group consisting of bovine serum albumin, human serum albumin and combinations thereof.

12. The method in accordance with claim 4, wherein said particles have diameters of between about 50 Å and about 20,000 Å.

13. The method in accordance with claim 12, wherein said particles have diameters of between about 50 Å and about 750 Å.

14. The method in accordance with claim 13, wherein said particles have diameters of between about 200 Å and about 400 Å.

15. The method in accordance with claim 14, wherein said microsphere shells have an average diameter between about 5,000 Å and about 40,000 Å.

16. The method in accordance with claim 4, wherein one or more particles are pegylated.

17. The method in accordance with claim 16, wherein said particles have diameters of between about 200 Å and about 400 Å.

18. The method in accordance with claim 14, wherein the albumin is selected from the group consisting of bovine serum albumin, human serum albumin and combinations thereof.

* * * * *